United States Patent [19]

Hirose et al.

[11] 4,376,780
[45] Mar. 15, 1983

[54] NOVEL PHENETHYLAMINE DERIVATIVES AND BRONCHDILATOR CONTAINING THE SAME

[75] Inventors: Noriyasu Hirose, Kokubunji; Shigeru Souda, Tokyo, both of Japan

[73] Assignee: Eisai Co., Ltd., Japan

[21] Appl. No.: 312,341

[22] Filed: Oct. 16, 1981

Related U.S. Application Data

[62] Division of Ser. No. 778,326, Mar. 16, 1977, Pat. No. 4,317,930.

[30] Foreign Application Priority Data

Mar. 19, 1976 [JP] Japan .................. 51-29175

[51] Int. Cl.³ .................. A01N 43/16; C07D 317/00
[52] U.S. Cl. .................. 424/282; 549/443
[58] Field of Search .................. 549/443; 424/282

[56] References Cited

U.S. PATENT DOCUMENTS

| | | | |
|---|---|---|---|
| 3,644,353 | 2/1972 | Lunts et al. | 564/364 X |
| 3,700,692 | 10/1972 | Suh et al. | 549/443 |
| 3,976,695 | 8/1976 | Kaiser et al. | 564/364 X |
| 4,317,930 | 3/1982 | Hirose et al. | 564/363 |

Primary Examiner—Robert V. Hines
Attorney, Agent, or Firm—Wenderoth, Lind and Ponack

[57] ABSTRACT

Novel phenethylamine derivatives represented by the general formula:

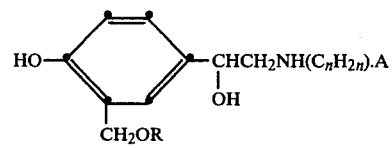

wherein R is a lower alkyl group, $C_nH_{2n}$ is a branched or straight alkylene group, A is a phenyl group unsubstituted or substituted with hydroxy, a lower alkoxy or a lower alkylene dioxy group, and n is an integer from 1 to 4, and pharmacologically acceptable acid addition salts thereof, and bronchdilator containing the same. These bronchdilator have an intense and durable bronchdilating effect and a weak heart stimulating action.

4 Claims, No Drawings

NOVEL PHENETHYLAMINE DERIVATIVES AND BRONCHDILATOR CONTAINING THE SAME

This is a divisional application of Ser. No. 778,326, filed Mar. 16, 1977 and now U.S. Pat. No. 4,317,930.

This invention relates to novel phenethylamine derivatives and bronchdilator containing said novel phenethylamine derivatives.

As the bronchdilators, there have been used Isoproterenol Isoetharine, Methoxyphenamine, Salbutamol, and the like. The inventors had studied to search compounds which may be used as the bronchdilator having a more intense and more durably bronchdilating effect, and less stimulating action to the heart than such prior bronchdilators, and finally accomplished this invention.

The phenethylamine derivative according to this invention is represented by the general formula (I):

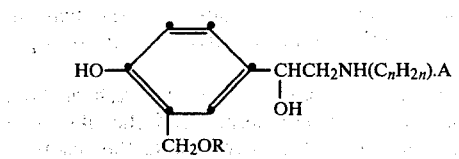

wherein R is a lower alkyl group, $C_nH_{2n}$ is a branched or straight alkylene group, A is a phenyl group unsubstituted or substituted with hydroxy, a lower alkoxy or a lower alkylene dioxy group, and n is an integer from 1 to 4.

The compound (I) according to this invention may be, if desired, converted into a pharmacologically acceptable acid addition salt thereof. As the pharmacologically acceptable acid addition salts, there are exemplified inorganic salts such as hydrochloride, hydrobromide, sulfate and the like; organic salts such as acetate, maleate, fumarate, citrate, succinate, oxalate, methane sulphonate, and the like.

The compounds (I) and the pharmacologically acceptable acid addition salts thereof act more selectively on the bronch-unstriated muscle to exhibit the bronchdilating effect, and they are $\beta$-adrenergics having weak heart stimulating action.

Accordingly, an object of this invention is to provide a novel phenethylamine derivative and pharmacologically acceptable acid addition salts thereof.

Another object of this invention is to provide a novel bronchdilator containing said phenethylamine derivative or a pharmacologically acceptable acid-addition salt thereof, which has intense and durable bronchdilating action.

Further objects of this invention will be more clearly understood from the following description.

An example of process for the production of the compound according to this invention is illustrated by the following chemical sequences:

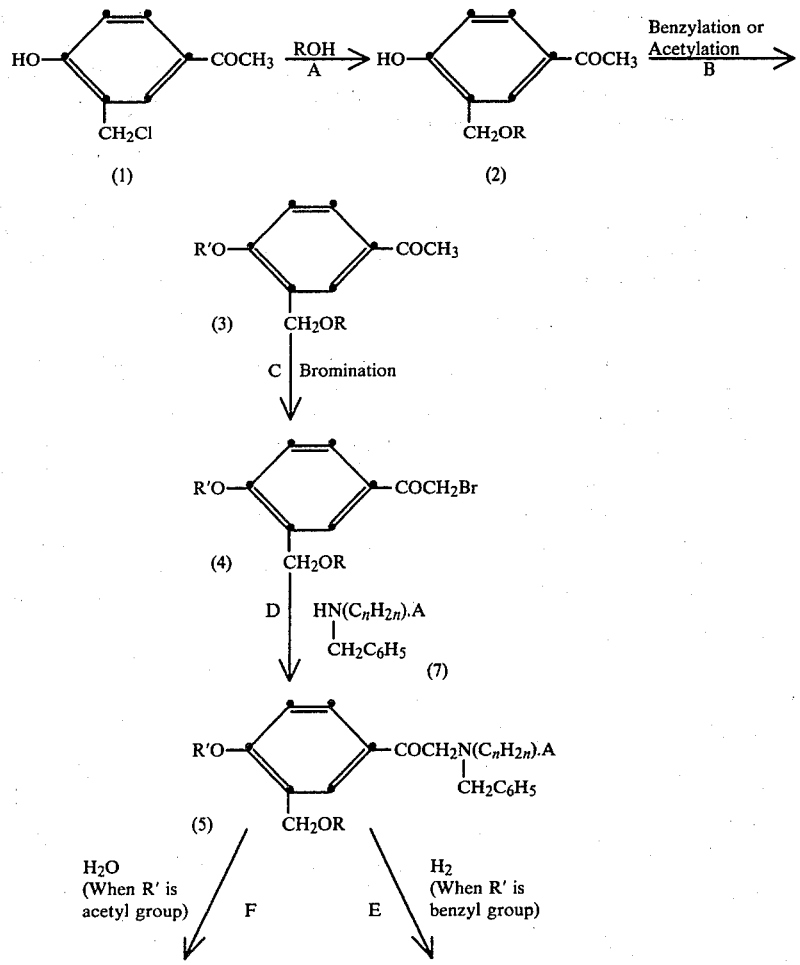

$$\text{HO}-\underset{\underset{\text{CH}_2\text{OR}}{|}}{\bigcirc}-\text{COCH}_2\text{N}(C_nH_{2n}).A \xrightarrow[G]{H_2} \text{HO}-\underset{\underset{\text{CH}_2\text{OR}}{|}}{\bigcirc}-\underset{\underset{\text{OH}}{|}}{\text{CHCH}_2\text{NH}}(C_nH_{2n}).A$$

(6)           -continued          (I)

wherein R, $C_nH_{2n}$ and A have the same meanings as mentioned above, and R represents benzyl or acetyl group.

Step A

3-Chloromethyl-4-hydroxy acetophenone (1) is reacted with a lower alcohol in the presence of an alkali reagent, to synthesize 3-lower alkoxymethyl-4-hydroxy acetophenone (2).

Step B

The compound (2) is subjected to a conventional benzylation or acetylation reaction, to synthesize 4-substituted 3-lower alkoxymethyl acetophenone (3).

Step C

The compound (3) is brominated to synthesize the corresponding bromoacetophenone compound (4).

Step D

The compound (4) is reacted with N-benzylamine compound (7) to synthesize the corresponding aminoketone compound (5).

Step E

When R' is benzyl group, the compound (5) is subjected to reduction reaction to obtain the compound (I) according to this invention.

Step F

When R' is acetyl group, the compound (5) is subjected to a conventional hydrolysis operation to synthesize the compound (6).

Step G

The compound (6) is subjected to reduction reaction to obtain the compound (I) according to this invention.

In the step A, a lower alcohol per se used in the reaction plays as the reaction solvent. It is preferable, in order to accelerate the reaction, to use an alkali reagent such as sodium bicarbonate, caustic alkalis and alkali carbonates, and sodium lower alkoxylates and the like corresponding to said lower alcohols used, as a de-acidizing agent.

In 4-benzylation reaction of the step B, there is used a reaction solvent, such as an alcoholic solvent, for example, methanol, ethanol and the like; and a ketone solvent, for example, methyl ethyl ketone, methylisobutyl ketone and the like. And, there is used a benzylation reagent, for example, benzylchloride, benzylbromide, and the like. In 4-acetylation, the reaction is effected in accordance with a conventional process for conversion of phenolic hydroxy group to the corresponding acetate.

In the step C, there is used a reaction solvent, such as a halogenous solvent, for example, chloroform, methylene chloride and the like; alcoholic solvent, for example, ethanol, methanol, isopropyl alcohol, and the like; and an ethereal solvent, for example, diethyl ether, dimethyl ether and the like.

As the brominating agent for the bromination, there is used a conventional bromination reagent, for example, bromine, cupric bromide, pyrolidone hydrotribromide and the like. Bromine is used in a form of bromine per se or in the presence of alminium chloride.

In the step D, there is used a reaction solvent, such as acetonitrile; an alcoholic solvent, for example, methanol, ethanol, isopropyl alcohol and the like; an estereal solvent, for example, ethyl acetate, and the like; an ethereal solvent, for example, diethyl ether, diisopropyl ether and the like.

It is preferable to use an alkali reagent such as alkali carbonates, pyridine, triethylamine and the like, as a de-acidizing agent in order to accelerate the reaction. Alternatively, an excess amount of N-benzylamine may be used as the de-acidizing agent.

In the step E, catalytic reduction is carried out in the presence of a catalyst, for example, palladium-carbon, platinum black, Raney nickel and the like at an ambient or elevated temperature under an atmospheric pressure or super pressure.

Alternatively, the reduction for de-benzylation may be carried out after the reduction of the carbonyl group using sodium borohydride, aluminium isopropoxide, lithium aluminium hydride and the like.

In the step F, hydrolysis is carried out using conventional acid hydrolyzing agent such as hydrochloric acid and the like.

In the step G, catalytic reduction is carried out in the presence of catalyst, such as palladium-carbon, platinum black, Raney nickel and the like, at an ambient or elevated temperature under an atmospheric pressure or super pressure.

The solvents to be used in the steps E, F and G are selected from alcoholic solvents consisting of methanol, ethanol, and isopropyl alcohol, and hydrous alcohols and the like.

The pharmacological action of the compounds according to this invention is illustrated by the following experiments.

In these experiments, the compounds according to this invention are examined, comparing with the control compounds, that is, Isoproterenol which is a typical $\beta$-adrenaline stimulant and Salbutamol which has a chemical structure similar to that of the compound according to this invention.

Compounds to be examined:

(i) Control compounds
L-isoproterenol hydrochloride—(hereinafter referred to isoproterenol)
Salbutamol hydrochloride: 1-(4-hydroxy-3-hydroxymethylphenyl)-2-(t-butylamino)-ethanol hydrochloride—(hereinafter referred to Salbutamol)

(ii) Compounds according to this invention:
1-(4-hydroxy-3-methoxymethylphenyl)-2-($\alpha$-methyl-4-methoxyphenethylamino)ethanol fumarate—(hereinafter referred to compound A of this invention)

1-(4-hydroxy-3-methoxymethylphenyl)-2-(α-methyl-3,4-methylene dioxyphenethylamine)ethanol oxalate—(hereinafter referred to compound B of this invention)

1-(4-hydroxy-3-methoxymethylphenyl)-2-(α-methyl-4-hydroxyphenethylamino)ethanol oxalate—(hereinafter referred to compound C of this invention)

Pharmacological Experiment 1

Protecting Effect Against The Dyspnea Caused By The Histamine

Male guinea pigs of Hartley strain were used. Aqueous solutions of the compounds to be examined were prepared in various concentrations, and administered orally to the guinea pigs, in a dose of 10 ml/Kg, respectively. After the oral administration, the guinea pigs were taken in a dome. Histamine solution in a concentration of 0.1% was sprayed through a nebulizer at a blow rate of 3500 ml/min. Two symptoms of hypoxia and fit of caughing were used as indices, and a probable appearing time of said two symptoms was watched and observed for 20 minutes from the start of the spraying.

The protecting effect was judged to be effective with the appearing time more than the double of the mean appearing time in 33 examples of the groups wherein physiological saline water was administered.

Results

TABLE 1

| | Isoproterenol | Salbutamol | Compound A of this invention | Compound B of this invention | Compound C of this invention |
|---|---|---|---|---|---|
| ED 50 (mg/Kg) | 2.90 | 2.25 | 0.39 | 0.56 | 0.36 |
| Ratio to isoproterenol | 100 | 129 | 744 | 518 | 806 |

Protecting effect on the asthmatous fit caused by the histamine spray

It was observed that the compounds A, B and C of this invention show the protecting effect on the fit with extremely small amount of the compounds, and these effects amounted to 5–7 times of those of two controls, salbutamol and isoproterenol. The durability action of the compounds A, B and C of this invention extended obviously longer than those of the two controls.

Pharmacological Experiment 2

Inhibitory Effect On The Increasing Reaction Of The Air-Way Resistance Of Histamine Normally healthy dogs (body weights were 10–15 Kg) were used as subject animals, and anesthetized with sodium pentobarbital urethane. The compounds to be examined were injected into the femoral vein of the dog. The inhibitory effect on the increasing reaction of the histamine (10 μg/Kg were administered) to the air way resistance was determined by Konzett-Rössler method.

Results

The compound A of this invention exhibited the inhibitory effect of more than 50% with 3 μg/Kg and also durability effect. This effects are almost same as those of salbutamol.

Although isoproterenol exhibited a distinct effect with about 1 μg/Kg immediately after the administration, but the effect decreased to only 10%, notwithstanding a large amount of administration such as 30 μg/Kg, after 10 minutes from the administration.

Pharmacological Experiment 3

Effect On The Heart Beat Numbers (1) Conscious guinea pigs

The guinea pigs were used, in which electrodes of stainless steel were pierced and put in both forelegs of the respective guinea pigs under previous anesthesia (after 24 hours from this operation).

The guinea pigs were isolated one by one in observation boxes, recorded their electrocardiogram (the first induction) under quiet circumstances, and heart beat numbers were counted.

All compounds to be examined were administered orally. The recording and measuring were carried out three times before the administration and with the lapse of time until 180 minutes after the administration.

Results

TABLE 2

| Compounds to be examined | Dosage (mg/Kg) | | |
|---|---|---|---|
| | 0.3 | 3 | 30 |
| Isoproterenol | 87.3 | 86.9 | 147.0 |
| Salbutamol | 33.2 | 33.6 | 94.0 |
| Compound A of this invention | 36.8 | 75.0 | 93.7 |

The increasing action to the heart beat numbers of the guinea pig

Calculation From The Product Of The Intensity Action With The Durability

The compound A of this invention showed a distinct increasing action to the heart beat numbers with the dosage of 0.3 mg/Kg. and showed variations corresponding to the dosage. The action of the compound A of this invention was relatively same as that of Salbutamol and weaker than that of Isoproterenol.

(2) Anesthetized dogs

Using anesthetized dogs as same as the pharmacological experiment 2, and injecting the compounds to be examined into the dogs from the femoral vein thereof, the increasing actions to the heart beat numbers were examined.

Results

The increasing action to the heart beat numbers of the anesthetized dogs was shown with the dosage more than 3 μg/Kg of the compound A of this invention through intravenous injection. This variation is weaker than that of Isoproterenol, and rather more intense than that of Salbutamol.

Pharmacological Experiment 4

Effect On The Blood Pressure

Using the anesthetized dogs as same as pharmacological experiment 2, and injecting the compounds to be examined into the dogs from the femoral vein, the effect on the blood pressure was examined.

Results

The effect on the blood pressure in the anesthetized dogs showed the remarkable depression effect upon the blood pressure with the dosage more than 3 μg/Kg of the compound A of this invention. Isoproterenol was relatively short in durability effect, but shows more intense depression effect than that of the compound A of this invention. The depression effect of Salbutanol had rather weaker tendency.

Pharmacological Experiment 5

Acute Toxicity

There was examined and observed the acute toxicity of the compounds to be examined for 7 days in the case of oral administration to mice.

Results

| Compounds to be examined | LD$_{50}$ (mg/Kg) |
|---|---|
| Compound A of this invention | 1050 |
| Compound B of this invention | 1200 |
| Compound C of this invention | 1200 |

It was found from the above pharmacological experiments that the compounds of this invention have very intense and durable bronchdilating action, and particularly, when administered orally, the action is more intense than those of Isoproterenol and Salbutamol. It is therefore considered that the compounds (I) of this invention and pharmacologically acceptable acid addition salts thereof are effective, as the bronchdilators, upon the treatment and the prevention for the bronchial asthma, the bronchial convulsion, the brounchoedema, the asthematic bronchitis, and the like, for example.

The dosage of the compound (I) of this invention and pharmacologically acceptable acid addition salts thereof may be varied from 0.1 to 300 mg and preferably from 10 to 100 mg a day for an adult, and it is desired to divisionally administer the compound (I) or salt with proper intervals in accordance with the symtom.

In this invention, the compound (I) and the pharmacologically acceptable acid addition salts thereof may be administered by a conventional method, that is, oral administration or parenteral administration such, for example, as injection, a nebulizer and the like. According to this invention, the compound (I) and the pharmacologically acceptable acid addition salts thereof may be administered with a sole substance per se, or as a preparation combined with a liquid or a solid carrier which does not affect the compound and the salt themselves. As a form of the preparation, there can be exemplified tablet, granule, powder, capsule, buccal, syrup, suspension or injection. The solid carriers capable of mixing with the compound (I) and the pharmacologically acceptable acid addition salts thereof include for example, corn starch, lactose, talc, carboxy methyl cellulose, crystalline cellulose, hydroxy propyl cellulose, stearic acid, calcium stearate, silicic anhydride, gum, and the like. The liquid carriers to be used for the suspension, the injection and the like include, for example, water, vegetable oil, various emusifying agents, various surfactants, and the like.

This invention will be more particularly illustrated by the following examples.

EXAMPLE 1

1-(4-hydroxy-3-methoxymethylphenyl)-2-(α-methyl-4-methoxyphenethylamino)-ethanol

Step A$_1$

Synthesis of 3-methoxymethyl-4-hydroxyacetophenone

An amount of 184.6 g of 3-chloromethyl-4-hydroxyacetophenone is dissolved in 923 ml of methanol, and the solution is stirred for 3 hours at room temperature after addition of 168 g of sodium bicarbonate. After the reaction is over, inorganics are filtered off, 3 l of water are added to the filtrate, and oily products isolated are extracted with toluene. The extracts are dried over anhydrous Glauber's salt, and the toluene is distilled off. The resulting crystals are recrystallized from diisopropyl ether.

Yield 147 g
Melting point 89°–90° C.

| Elementary analysis of the product for C$_{10}$H$_{12}$O$_3$ gives: | | |
|---|---|---|
| | C | H |
| Calculated (%) | 66.64 | 6.73 |
| Found (%) | 66.71 | 6.72 |

Step B$_1$

Synthesis of 4-benzyloxy-3-methoxymethyl-acetophenone

To 2 l of ethanol, there are added 200 g of the compound obtained in the step A$_1$, 154.5 g of benzylchloride, 184 g of anhydrous potassium carbonate and a small amount of potassium iodide. The mixture is boiled for 6 hours with stirring. Inorganics are filtered off and the filtrate is concentrated. The resulting oily products are dissolved in toluene, and the solution is washed with water, dried and distilled under vacuum.

Boiling point 175°–178° C. (0.5 mm/Hg)
Yield 293 g

| Elementary analysis of the product for C$_{17}$H$_{18}$O$_3$ gives: | | |
|---|---|---|
| | C | H |
| Calculated (%) | 75.53 | 6.71 |
| Found (%) | 75.42 | 6.90 |

Step C$_1$

Synthesis of 4-benzyloxy-3-methoxymethyl-α-bromoacetophenone

Amounts of 200 g of the compound obtained in the step B$_1$ and 13 g of benzoyl peroxide are dissolved in 2 l of ethanol, and the solution is maintained at a temperature from 15° to 20° C. To this solution, 215 g of bromine are added dropwise with stirring. After the addition was over, the solution is stirred for one hour. The crystals precipitated are recovered by filtration, and recrystallized from ethanol.

Yield 178 g
Melting point 94°–96° C.

| Elementary analysis of the product for C$_{17}$H$_{17}$O$_3$Br gives: | | |
|---|---|---|
| | C | H |
| Calculated (%) | 58.46 | 4.92 |

-continued

| Elementary analysis of the product for $C_{17}H_{17}O_3Br$ gives: | | |
|---|---|---|
| | C | H |
| Found (%) | 58.42 | 5.10 |

Step D₁

Synthesis of 4-benzyloxy-3-methoxymethyl-α[N-benzyl-N(α-methyl-4-methoxyphenethyl)amino]acetophenone Amounts of 39.5 g of the compound obtained in the step C₁ and 57.7 g of N-benzyl-N(α-methyl-4-methoxyphenethyl)amine are stirred for 6 hours in 200 ml of acetonitrile. The crystals precipitated are filtered off, and the filtrate is concentrated, to give the object compound. The compound is used for the following step without purification.

Step E₁ a Synthesis of 1-(4-benzyloxy-3-methoxymethylphenyl)-2-[N-benzyl-N(α-methyl-4-methoxyphenethyl)]amino-ethanol An amount of 14.2 of the compound obtained in the step D₁ is dissolved in 70 ml of ethanol. This solution is added dropwise with stirring to a solution which was prepared by dissolving 4.1 g of sodium borohydride in 70 ml of ethanol. After stirring for two hours at room temperature, the ethanol is distilled off. After adding water, the residue is extracted with toluene, washed with water and dried. The toluene is then distilled off. The resulting oily products are crystallized as the hydrochloride and recrystallized from acetonitrile.
Yield 12.4 g
Melting point 183.0°–183.5° C.

| Elementary analysis of the product for $C_{34}H_{39}NO_4 \cdot HCl$ gives: | | | |
|---|---|---|---|
| | C | H | N |
| Calculated (%) | 72.63 | 7.18 | 2.49 |
| Found (%) | 72.38 | 7.14 | 2.41 | b Synthesis of 1-(4-hydroxy-3-methoxymethylphenyl)-2-(α-methyl-4-methoxyphenethylamino)ethanol An amount of 8.5 g of the corresponding free amine which is produced by treating the compound obtained in the above item a with sodium hydroxide, is dissolved in 85 ml of ethanol, and the solution is reduced catalytically in the presence of 5% palladium-carbon under an atmospheric pressure.

After filtering off the catalyst, the solvent of the filtrate is distilled off. The residue is recrystallized from diisopropyl ether, to give the object compound in the form of needle crystal.

| Yield | | 5.9 g | |
|---|---|---|---|
| N.M.R. | (CDCl₃, TMS) | | |
| δ: | 7.2–6.8 ppm | (7H, m, aromatic H) | |
| | 4.62 | (2H, s, CH₂OCH₃) | |
| | 4.50 | (1H, m, —CH—CH₂) with OH | |
| | 4.2–3.6 | (3H, broad, 2-OH and NH) | |
| 3.80 | (3H, s, 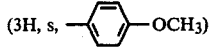—OCH₃) | | |
| 3.42 | (3H, s, CH₂OCH₃) | | |
| 3.0–2.7 | (5H, m, —CH₂N—CH—CH₂—) | | |
| 1.40 | (3H, d, —CH—CH₃) | | |

The object compound (free amine) obtained in the above item b may form crystalline salts with various acids.
The corresponding fumarate:
Melting point 165° C. (with decomposition)

| Elementary analysis of the product for $C_{20}H_{27}NO_4 \cdot \frac{1}{2}C_4H_4O_4$ | | | |
|---|---|---|---|
| | C | H | N |
| Calculated (%) | 65.48 | 7.26 | 3.47 |
| Found (%) | 65.29 | 7.22 | 3.35 |

The corresponding hydrochloride:
Melting point 126°–127.5° C.
The corresponding oxalate:
Melting point 190.5° C. (with decomposition)

EXAMPLE 2

1-(4-hydroxy-3-methoxymethylphenyl)-2-(α-methyl-3,4-methylenedioxy-phenethylamino)ethanol

Step B₂

Synthesis of 4-acetoxy-3-methoxymethyl-acetophenone

Amounts of 55 g of 4-hydroxy-3-methoxymethyl-acetopenone obtained in the step A₁ of the Example 1, 260 ml of acetic anhydride, and 10 ml of pyridine are mixed, and the mixture is heated under reflux for 4 hours. After removing the acetic anhydride and the pyridine by conventional process, the reaction mixture is distilled under reduced pressure.
Boiling point 139°–142° C. (0.8 mm/Hg)
Yield 54 g

| Elementary analysis of the product for $C_{12}H_{14}O_4$ gives: | | |
|---|---|---|
| | C | H |
| Calculated (%) | 64.85 | 6.35 |
| Found (%) | 65.02 | 6.26 |

Step C₂

Synthesis of 4-acetoxy-3-methoxymethyl-α-bromo-acetophenone

An amount of 10 g of the compound obtained in the above step B₂ is dissolved in 200 ml of chloroform. Maintaining the reaction temperature at 10° C., 7.2 g of bromine are added dropwise to the solution with stirring. After stirring for two hours at room temperature, the reaction mixture is washed with water, dried and distilled under reduced pressure.
Boiling point 173°–173.5° C. (0.8 mm/Hg)
Yield 7.5 g

| Elementary analysis of the product for $C_{12}H_{13}O_4Br$ gives: | | |
|---|---|---|
| | C | H |
| Calculated (%) | 47.84 | 4.36 |
| Found (%) | 47.68 | 4.35 |

Step $D_2$

Synthesis of
4-acetoxy-3-methoxymethyl-α[N-benzyl-N(α-methyl-3,4-methylenedioxyphenethyl)amino]acetophenone Amounts of 17.3 g of the compound obtained in the above step $C_2$ and 31.0 g of N-benzyl-N-(α-methyl-3,4-methylenedioxyphenethyl)amine are stirred for 5 hours in 230 ml of acetonitrile. After-treatment is achieved in the same manner with the step $D_1$. The product is used for the following step without purification.

Step $F_2$

Synthesis of
4-hydroxy-3-methoxymethyl-α[N-benzyl-N(α-methyl-3,4-methylenedioxyphenethyl)amino]acetophenone An amount of 22 g of the compound obtained in the above step $D_2$ is dissolved in 150 ml of 6 N hydrochloric acid, and the solution is allowed to stand for 10 hours at room temperature. The crystals precipitated are recovered by filtration, and recrystallized from isopropyl alcohol, to form the hydrochloride mono-hydrate of the object compound.

Yield 17 g
Melting point 219° C. (with decomposition)

| Elementary analysis of the product for $C_{27}H_{30}NO_5 \cdot HCl$ gives: | | | |
|---|---|---|---|
| | C | H | N |
| Calculated (%) | 64.59 | 6.43 | 2.79 |
| Found (%) | 64.30 | 6.21 | 2.75 |

Step $G_2$

Synthesis of
1-(4-hydroxy-3-methoxymethylphenyl)-2-(α-methyl-3,4-methylenedioxyphenethylamino)ethanol An amount of 7.7 g of the hydrochloride obtained in the step $F_2$ is dissolved in 80 ml of methanol, and the solution is subjected to the hydrogenolysis in the presence of palladium-carbon in accordance with the Example 1 (Step $E_1$, b). The reactants are then alkalified with aqueous ammonia. The object compound is extracted with ether.

The object compound is crystallized as the oxalate, which is purified by recrystallizing from aqueous methanol.

Yield 4.5 g
Melting point 202.5° C. (with decomposition)

| Elementary analysis of the product for $C_{20}H_{25}NO_5 \cdot \frac{1}{2}C_2H_2O_4$ gives: | | | |
|---|---|---|---|
| | C | H | N |
| Calculated (%) | 62.35 | 6.49 | 3.46 |
| Found (%) | 62.59 | 6.49 | 3.62 |
| NMR(DMSO-$d_6$, TMS) | | | |
| δ: 4.41 ppm (2H, s, $CH_2OCH_3$) | | | |
| 3.35 (3H, s, $CH_2OCH_3$) | | | |

EXAMPLE 3

1-(4-hydroxy-3-methoxymethylphenyl)-2-(α-methyl-4-hydroxy-phenethylamino)ethanol

Step $D_3$

Synthesis of
4-acetoxy-3-methoxymethyl-α[N-benzyl-N(α-methyl-4-benzyloxyphenethyl)amino]acetophenone An amount of 12.0 g of the compound obtained in the step $C_2$ is condensed with 26.4 g of N-benzyl-N(α-methyl-4-benzyloxyphenethyl)amine in accordance with the step $D_2$ in the Example 2. The resulting product is used for the following step, without purification.

Step $F_3$

Synthesis of
4-hydroxy-3-methoxymethyl-α[N-benzyl-N(α-methyl-4-benzyloxyphenethyl)amino]acetophenone An amount of 16.6 g of the compound obtained in the step $D_3$ of the Example 2 is treated with concentrated hydrochloric acid in accordance with the step $F_2$ of the Example 2. The product is recrystallized from ethanol, to give the hydrochloride of the object compound as colorless crystalline masses.

Yield 12 g
Melting point 108° C.

| Elementary analysis of the product for $C_{33}H_{35}NO_4 \cdot HCL$ gives: | | | |
|---|---|---|---|
| | C | H | N |
| Calculated (%) | 72.57 | 6.65 | 2.56 |
| Found (%) | 72.60 | 6.57 | 2.56 |

Step $G_3$

Synthesis of
1-(4-hydroxy-3-methoxymethylphenyl)-2-(α-methyl-4-hydroxy-phenethylamino)ethanol An amount of 3.9 g of the compound obtained in the step $F_3$ is dissolved in 40 ml of methanol, and the solution is subjected to reduction reaction in the presence of palladium-carbon catalyst in accordance with the step $G_2$.

The resulting object compound is made to ½ equivalent oxalate and crystallized.

Yield 2.1 g
Melting point 158°–160° C.

| Elementary analysis of the product for $C_{19}H_{25}NO_4 \cdot \frac{1}{2}C_2H_2O_4$ gives: | | | |
|---|---|---|---|
| | C | H | N |
| Calculated (%) | 63.80 | 6.97 | 3.72 |
| Found (%) | 63.74 | 6.92 | 3.52 |
| NMR(DMSO-$d_6$, TMS) | | | |
| δ: 4.39 ppm (2H, s, $CH_2OCH_3$) | | | |
| 3.32 (3H, s, $CH_2OCH_3$) | | | |

The following Table 3 shows examples wherein the compounds according to this invention are listed.

TABLE 3

$$HO-\underset{CH_2OR}{\underset{|}{\bigcirc}}-\underset{\underset{H}{|}}{C}HCH_2NH(C_nH_{2n})A \quad (I)$$

| Example | R | ($C_nH_{2n}$) | A | Appearance | Molecular Formula Melting Point (°C.) | C | H | N |
|---|---|---|---|---|---|---|---|---|
| 4 | $CH_3$ | $-C(CH_3)_2-CH_2-$ | $-\bigcirc$ | Fine needle | $C_{20}H_{27}NO_3.HCl$ 185–186 | 65.63 65.56 | 7.72 7.76 | 3.82 3.73 |
| 5 | $C_2H_5$ | $-C(CH_3)_2-CH_2-$ | $-\bigcirc$ | Fine needle | $C_{21}H_{29}NO_3.HCl$ 160–161 | 66.38 66.56 | 7.97 8.10 | 3.69 3.37 |
| 6 | $CH_3$ | $-CH\begin{smallmatrix}CH_3\\ \\CH_2-\end{smallmatrix}$ | $-\bigcirc$ | Fine needle | $C_{19}H_{25}NO_3.HCl$ 152–153.5 | 64.84 64.67 | 7.46 7.40 | 3.98 3.87 |
| 7 | $C_2H_5$ | $-CH\begin{smallmatrix}CH_3\\ \\CH_2-\end{smallmatrix}$ | $-\bigcirc$ | Fine needle | $C_{20}H_{27}NO_3.HCl$ 167.5 (with decomposition) | 65.63 65.39 | 7.72 7.70 | 3.82 3.79 |

EXAMPLE 8

Tablet For Oral Administration

| | |
|---|---|
| 1-(4-hydroxy-3-methoxymethylphenyl)-2-(α-methyl-4-methoxyphenethylamino)-ethanol fumarate | 5 g |
| Lactose | 30 g |
| Corn starch | 50 g |
| Carboxy methyl cellulose | 10 g |
| Crystalline cellulose | 4.5 g |
| Magnesium stearate | 0.5 g |

Using the above formulation and according to a conventional process, tablets are prepared, in which 5 mg of 1-(4-hydroxy-3-methoxymethylphenyl)-2-(α-methyl-4-methoxyphenethylamino)ethanol fumarate per tablet are contained.

EXAMPLE 9

Injection

| | |
|---|---|
| 1-(4-hydroxy-3-methoxymethylphenyl)-2-(α-methyl-4-hydroxyphenethylamino)-ethanol oxalate | 5 g |
| Distilled water for injection sufficient to make up the total to | 10 l |

The injection is prepared using the above formulation and according to a conventional process. Said injection is packed into ampoules in an amount of 2 ml, respectively. Thus, each ampoule contains 1 mg of 1-(4-hydroxy-3-methoxymethylphenyl)-2-(α-methyl-4-hydroxy-phenethylamino)ethanol oxalate.

EXAMPLE 10

Inhalant

| | |
|---|---|
| 1-(4-hydroxy-3-methoxymethylphenyl)-2-(α-methyl-4-methoxyphenethylamino)-ethanol fumarate | 2.0 g |
| Chlorobutanol | 0.5 g |
| Citric acid | 1.0 g |
| Sodium hydroxide | 0.375 g |
| purified water sufficient to | |

| -continued | |
|---|---|
| make up the total to | 100 ml |

The inhalant is prepared using the above formulation and according to a conventional process. This inhalant is used for a spray inhalation treatment by means of aerosol, a nebulizer, and the like.

What is claimed is:

1. A phenethylamine derivative represented by the general formula:

$$HO-\underset{CH_2OR}{\underset{|}{\bigcirc}}-\underset{\underset{OH}{|}}{C}HCH_2NH(C_nH_{2n}).A$$

wherein R is a lower alkyl group, $C_nH_{2n}$ is a branched or straight alkylene group, A is a phenyl group substituted with a lower alkylene dioxy group, and n is an integer from 1 to 4, and a pharmacologically acceptable acid-addition salt thereof.

2. The phenethylamine derivative according to the claim 1, which is a compound represented by the formula:

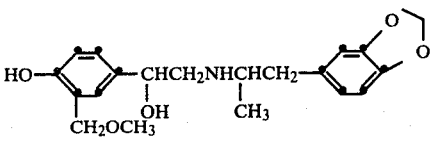

3. A bronchdilator, comprising a bronchdilating amount of a phenethylamine derivative represented by the general formula:

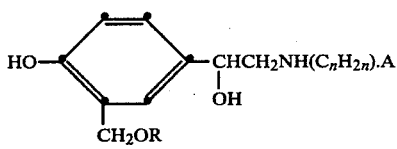
wherein R is a lower alkyl group, $C_nH_{2n}$ is a branched or straight alkylene group, A is a phenyl group substituted with a lower alkylene dioxy group, and n is an integer from 1 to 4, or a pharmacologically acceptable acid-addition salt thereof.
4. The bronchdilator according to the claim 3, wherein the phenethylamine derivative is a compound represented by the formula:
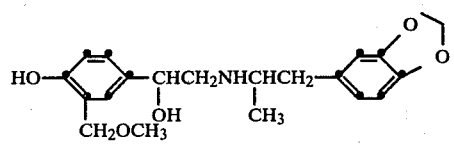
* * * * *